US009758568B2

(12) United States Patent
Grillberger et al.

(10) Patent No.: US 9,758,568 B2
(45) Date of Patent: Sep. 12, 2017

(54) OLIGOPEPTIDE-FREE CELL CULTURE MEDIA

(71) Applicants: Baxalta Incorporated, Bannockburn, IL (US); Baxalta GmbH, Glattpark (Opfikon) (CH)

(72) Inventors: Leopold Grillberger, Vienna (AT); Manfred Reiter, Vienna (AT); Wolfgang Mundt, Vienna (AT); Artur Mitterer, Orth/Donau (AT)

(73) Assignees: Baxalta GmbH, Glattpark (Opfikon) (CH); Baxalta Incorporated, Bannockburn, IL (US)

( * ) Notice: Subject to any disclaimer, the term of this patent is extended or adjusted under 35 U.S.C. 154(b) by 0 days.

(21) Appl. No.: 14/942,771

(22) Filed: Nov. 16, 2015

(65) Prior Publication Data
US 2016/0068587 A1 Mar. 10, 2016

Related U.S. Application Data

(63) Continuation of application No. 13/035,696, filed on Feb. 25, 2011, now abandoned, which is a continuation of application No. 11/649,694, filed on Jan. 3, 2007, now abandoned.

(60) Provisional application No. 60/756,419, filed on Jan. 4, 2006.

(51) Int. Cl.
C12N 1/00 (2006.01)
C07K 14/755 (2006.01)
C12N 7/00 (2006.01)
C12N 5/00 (2006.01)

(52) U.S. Cl.
CPC ............ *C07K 14/755* (2013.01); *C12N 5/005* (2013.01); *C12N 5/0018* (2013.01); *C12N 7/00* (2013.01); *C12N 2500/05* (2013.01); *C12N 2500/10* (2013.01); *C12N 2500/20* (2013.01); *C12N 2500/24* (2013.01); *C12N 2500/32* (2013.01); *C12N 2500/38* (2013.01); *C12N 2500/46* (2013.01); *C12N 2500/50* (2013.01); *C12N 2710/24151* (2013.01)

(58) Field of Classification Search
None
See application file for complete search history.

(56) References Cited

U.S. PATENT DOCUMENTS

| | | |
|---|---|---|
| 4,431,629 A | 2/1984 | Olsen |
| 4,443,540 A | 4/1984 | Chervan et al. |
| 4,657,866 A | 4/1987 | Kumar |
| 4,767,704 A | 8/1988 | Cleveland et al. |
| 4,978,616 A | 12/1990 | Dean, Jr. et al. |
| 5,045,468 A | 9/1991 | Darfler |
| 5,122,469 A | 6/1992 | Mather et al. |
| 5,316,938 A | 5/1994 | Keen et al. |
| 5,378,612 A | 1/1995 | Nakashima et al. |
| 5,393,668 A | 2/1995 | Cinatl et al. |
| 5,441,868 A | 8/1995 | Lin |
| 5,445,956 A | 8/1995 | Hammock et al. |
| 5,498,599 A | 3/1996 | Choi et al. |
| 5,573,937 A | 11/1996 | Shinmoto et al. |
| 5,633,162 A | 5/1997 | Keen et al. |
| 5,719,050 A | 2/1998 | Hashimoto et al. |
| 5,741,705 A | 4/1998 | Blom et al. |
| 5,789,247 A | 8/1998 | Ballay et al. |
| 5,804,420 A | 9/1998 | Chan et al. |
| 5,811,299 A | 9/1998 | Renner et al. |
| 5,840,719 A | 11/1998 | Rubin et al. |
| 5,851,800 A | 12/1998 | Adamson et al. |
| 5,885,835 A | 3/1999 | Blom et al. |
| 6,048,728 A | 4/2000 | Inlow et al. |
| 6,100,061 A | 8/2000 | Reiter et al. |
| 6,475,725 B1 | 11/2002 | Reiter et al. |
| 6,537,782 B1 | 3/2003 | Shibuya et al. |
| 6,596,526 B1 | 7/2003 | Plaimauer et al. |
| 6,936,441 B2 | 8/2005 | Reiter et al. |
| 7,094,574 B2 | 8/2006 | Reiter et al. |
| 2002/0182679 A1 | 12/2002 | Reiter et al. |
| 2003/0017548 A1 | 1/2003 | Martin et al. |
| 2003/0073116 A1 | 4/2003 | Ginsburg et al. |
| 2003/0104527 A1 | 6/2003 | Figueira et al. |

(Continued)

FOREIGN PATENT DOCUMENTS

| | | |
|---|---|---|
| AT | 1659/99 | 9/1999 |
| AU | 78958/98 | 10/1998 |

(Continued)

OTHER PUBLICATIONS

"Technical Resources: 32500—DMEM/F-12, powder." Available online at http://www.lifetechnologies.com/us/en/home/technical-resources/media-formulation.218.html. Accessed Aug. 3, 2016. 2 pages.*
"32500—DMEM/F-12, powder." Life Technologies Technical Resources. Available online at <http://www.lifetechnolgies.com/us/en/home/technical-resources/media-formulation.218.html>. accessed Jan. 9, 2014. 3 pages.
Assignment document for U.S. Appl. No. 60/756,419, filed Jan. 4, 2006.
AstraZeneca AB Opposition Brief to European Patent No. 1200561, dated Mar. 14, 2007.
Bayer Healthcare AG Opposition Brief to European Patent No. 1200561, dated Mar. 13, 2007.
BD Bionutrients™; Technical Manual Advanced Bioprocessing Third Edition Revised Oct. 2006, pp. 1-67.

(Continued)

*Primary Examiner* — Allison Fox
(74) *Attorney, Agent, or Firm* — Morgan, Lewis & Bockius LLP; Christopher J. Betti

(57) ABSTRACT

The present invention relates to oligopeptide-free cell culture media comprising at least 0.5 mg/L of a polyamine and to methods for cultivating cells in said oligopeptide-free cell culture media comprising at least 0.5 mg/L of a polyamine. The invention also relates to methods for expressing at least one protein in a medium comprising at least 0.5 mg/L of a polyamine and to methods for producing at least one virus in a medium comprising at least 0.5 mg/L of a polyamine.

10 Claims, 7 Drawing Sheets

(56) References Cited

U.S. PATENT DOCUMENTS

2003/0203448 A1 10/2003 Reiter et al.
2005/0272124 A1 12/2005 Chen et al.

FOREIGN PATENT DOCUMENTS

| | | |
|---|---|---|
| AU | 199953636 | 3/2001 |
| CA | 2161517 | 11/1994 |
| CN | 1210866 | 3/1999 |
| EP | 0 160 457 | 11/1985 |
| EP | 0 481 791 | 4/1992 |
| EP | 0 481 792 | 4/1992 |
| EP | 0 485 689 | 5/1992 |
| EP | 0 631 731 | 1/1995 |
| EP | 0 659 880 | 6/1995 |
| EP | 0 666 312 | 8/1995 |
| EP | 0 711 835 | 5/1996 |
| EP | 0 872 487 | 10/1998 |
| EP | 0 120 896.6 | 9/2000 |
| EP | 0 121 1878 | 8/2001 |
| EP | 1 200 561 | 6/2006 |
| FR | 2 196 386 | 3/1974 |
| JP | 3-244391 | 10/1991 |
| JP | 4-316484 | 11/1992 |
| JP | 5-123178 | 5/1993 |
| JP | 7-039386 | 2/1995 |
| JP | 2-859679 | 2/1999 |
| JP | H01-211488 | 8/1999 |
| WO | 85/02610 | 6/1985 |
| WO | 86/04920 | 8/1986 |
| WO | 88/00967 | 2/1988 |
| WO | 89/00192 | 1/1989 |
| WO | 91/09122 | 6/1991 |
| WO | 91/10726 | 7/1991 |
| WO | 94/25599 | 11/1994 |
| WO | 96/07730 | 3/1996 |
| WO | 96/15231 | 5/1996 |
| WO | 96/18734 | 6/1996 |
| WO | 96/26266 | 8/1996 |
| WO | 96/40866 | 12/1996 |
| WO | 97/05240 | 2/1997 |
| WO | 98/08934 | 3/1998 |
| WO | 98/15614 | 4/1998 |
| WO | 98/54296 | 12/1998 |
| WO | 99/05268 | 2/1999 |
| WO | 99/47648 | 9/1999 |
| WO | 99/57246 | 11/1999 |
| WO | 00/03000 | 1/2000 |
| WO | 01/11021 | 2/2001 |
| WO | 01/14529 | 3/2001 |
| WO | 01/23527 | 4/2001 |
| WO | 02/24876 | 3/2002 |
| WO | 02/101019 | 12/2002 |
| WO | 03/029442 | 4/2003 |
| WO | 2004/005493 | 1/2004 |
| WO | 2005/035748 | 4/2005 |
| WO | 2006/026445 | 3/2006 |
| WO | 2006/045438 | 5/2006 |

OTHER PUBLICATIONS

Berg, D.T. et al., "High-Level Expression of Secreted Proteins from Cells Adapted to Serum-Free Suspension Culture"; Bio Techniques; 1993; Vo. 14(6); pp. 972-978.
Bielicki, J. et al., "Recombinant Human Sulphamidase: Expression, Amplification, Purification and Characterization"; 1998; Biochem. J.; vol. 329; pp. 145-150.
Bioceuticals Arzneimittel AG Opposition Brief to European Patent No. 1200561, dated Mar. 14, 2007.
Biogen IDEC MA, Inc. Opposition Brief to European Patent No. 1200561, dated Mar. 14, 2007.
Bottenstein et al., "Growth of a rat neuroblastoma cell line in serum-free supplemented medium," PNAS, 76(1):514-517 (1979).
Brown, M.E. et al., "Process Development for the Production of Recombinant Antibodies Using the Glutamine Synthetase (GS) System"; 1992; Cytotechnology; vol. 9; pp. 231-236.
Burger, C. et al., "An Integrated Stragey for the Process Development of a Recombinant Antibody-Cytokine Fusion Protein Expressed in BHK Cells"; 1999; Appl. Microbiol. Biotechnol.; vol. 52; pp. 345-353.
Campina Nederland Holding B.V. Opposition Brief to European Patent No. 1220893, dated Mar. 21, 2007.
Cartier, M. and Stanners, C.P., "Stable, High-Level Expression of a Carcinoembryonic Antigen-encoding cDNA After Transfection and Amplification with eh Dominant and Selectable Asparagine Synthetase Marker"; 1990; Gene; col. 95; pp. 223-230.
Chen et al., "A low-cost chemically defined protein free medium for a recombinant CHO cell line producing prothrombin," Biotechnology Letters, vol. 22, pp. 837-841 (2000).
Chen, Zhonggang, "Section III. The functions of ployamines in the synthesis of biological macromolecules," 1998, Feed Study, No. 5, pp. 16-19.
Childs et al., "Polyamine-dependent gene expression," Cell. Mol. Life Sci., 60(7):1394-1406 (2003).
Cole, E.S. et al., "Recombinant Human Thyroid Stimulating Hormone: Development of a Biotechnology Product for Detection of Metastatic Lesions of Thyroid Carcinoma"; Sep. 1993; Biotechnology; vol. 11; pp. 1014-1024.
Cruz, H.J. et al., "Adaptation of BHK Cells Producing a Recombinant Protein to Serum-Free Media and Protein-Free Medium"; 1998; Cytotechnology; vol. 26; pp. 59-64.
Datasheet for 32500 DMEM/F-12 Powder, Life Technologies, downloaded on Dec. 19, 2014.
Declaration of Dr. Ricardo Matanguihan in support of Maxygen, Inc. Opposition Brief to European Patent No. 1220893, dated Mar. 20, 2007 (including Annexes A and B).
Declaration of Dr. Ruediger Heidemann in support of Maxygen, Inc. Opposition Brief to European Patent No. 1220893, dated Mar. 20, 2007 (including Annexes A-F).
Deltown Specialties; Peptone Selection Guide for Diagnostic and Fermentation Nutrients, 1994, 4 pages.
Donaldson, M.S. and Sculer M.L., "Low-Cost Serum-Free Medium for the BTI-Tn5B1-4 Insect Cell Line"; 1998; Biotechnol. Prog.; vol. 14; pp. 573-579.
Doyle, A. et al. eds., "Cloning," Part 4D Module 4D1 In Cell & Tissue Culture: Laboratory Procedures; 1998; John Wiley & Sons; London; Cloning Techniques (Non-hybridoma Related); pp. 4D:1.1-4D:1.9.
Eagle, H., "Amino Acid Metabolism in Mammalian Cell Cultures"; Aug. 21, 1939; Science; vol. 130; pp. 432-437.
European Search Report from EP 12160789, dated Oct. 2, 2012 (3 pages).
Extract from Hauser, H. and Wagner, R. eds.; Mammalian Cell Biotechnology in Protein Production; 1997; Walter de Gruyter, Berlin; pp. 33-137.
Farrell, P.J. et al., "High-Level Expression of Secreted Glycoproteins in Transformed Lepidopteran Insect Cells Using a Novel Expression Vector"; Dec. 20, 1998; Biotechnology and Bioengineering; vol. 60(6); pp. 656-663.
Faure, T. et al., "Stable Expression of Coagulation Factors FVIII and Fix in Recombinant Chinese Hamster Ovary Cells"; 1989; Meeting Info. 9th General Meeting of the European Society for Animal Cell Technology; Knokke (Belgium); 1988; pp. 481-488.
F. Hoffmann-LaRoche AG Opposition Brief to European Patent No. 1200561, dated Mar. 13, 2007.
F. Hoffmann-La Roche AG Opposition Brief to European Patent No. 1220893, dated Mar. 27, 2007.
Field, R.P. et al., "Production of a Chimeric Antibody for Tumour Imaging and Therapy From Chinese Hamster Ovary (CHO) and Myeloma Cells"; May 1990; Proceedings fo the 10th ESACT Meeting; pp. 742-744.
Fischer, B. et al., "Comparison of N-Glycan Pattern of Recombinant Human Coagulation Factors II and IX Expressed in Chinese Hamster Ovary (CHO) and African Green Monkey (Vero) Cells"; 1996; J. Thrombos. and Trombolys. ; vol. 3; pp. 57-62.

(56) References Cited

OTHER PUBLICATIONS

Fischer, B.E. et al., "Biochemical and Functional Characterization of Recombinant von Willebrand Factor Produced on a Large Scale"; 1997; CMLS; vol. 53; pp. 943-950.

Fischer, B.E. et al., "Structural Analysis of Recombinant von Willebrand Factor Produced at Industrial Scale Fermentation of Transformed CHO Cells Co-expressing Recombinant Furin"; 1995; FEBS Letters; vol. 375; pp. 259-262.

Fischer et al., "Structural Analysis of Recombinant von Willebrand Factor: Identification of Hetero- and Homo-Dimers"; 1994; FEBS Letters; vol. 351; pp. 345-348.

Franek, F. et al., "Plant Protein Hydrolysates: Preparation of Defined Peptide Fractions Promoting Growth and Production in Animal Cells Cultures"; 2000; Biotechnol. Prog.; vol. 16; No. 5; pp. 688-692.

Fraslon et al., "Culture of fetal alveolar epithelial type II cells in serum-free medium," In Vitro Cell Dev. Biol., 27(11) 843-852 (1991).

Freshney, R.I., "The Culture Environment: Substrate, Gas Phase, Medium, and Temperature"; Chapter 7 in Culture of Animal Cells a Manual of Basic Technique, 2nd Edition; 1987; pp. 57-84.

Friedman, J.S. et al., "High Expression in Mammalian Cells Without Amplication"; Apr. 1989; Biotechnology; vol. 7; pp. 359-362.

Fusi et al., "Effects of putrescine, cadaverine, spermine, spermidine and β-phenylethylamine on cultured bovine mammary epithelial cells," Italian Journal of Animal Science, vol. 7, pp. 131-140 (2008).

Gaboriau et al., "Polyamine modulation of iron uptake in CHO cells," Biochem. Pharmacol., 67(9):1629-1637 (2004).

Gandor, C., "Amplification and Expression of Recombinant Genes in Serum-Independent Chinese Hamster Ovary Cells"; FEBS Letters; vol. 377; pp. 290-294.

Ganne et al., "Application of statistical design of experiments to the optimization of factor VIII expression by CHO cells," Cytotechnology, vol. 6, pp. 233-240 (1991).

GIBCO™ Saibo bayiyo catalog (Cell culture catalog), 2003-2004, pp. 24-28, 33-36 and 43-45 (2003).

Gorfein, S.F. et al., "Recombinant Protein Production by CHO Cells Cultured in a Chemically Defined Medium"; 1996; presented at JAACT, Yokohama: Japan; 16 pages.

Grillberger et al., "Emerging trends in plasma-free manufacturing of recombinant protein therapeutics expressed in mammalian cells," Biotechnology Journal, vol. 4, pp. 186-201.

Haldankar, R. et al., "Stable Production of a Human Growth Hormone Antagonist From CHO Cells Adapted to Serum-Free Suspension Culture"; 1999; Biotechnol. Prog.; vol. 15(3); pp. 336-349.

Ham et al., "Putrescine and Related Amines as Growth Factors for a Mammalian Cell Line," Biochem Biophys Res Commun., 14(1): 34-38.

Ham, R.G., "Clonal Growth of Mammalian Cells in a Chemically Defined, Synthetic Medium"; 1965; PNAS; vol. 53; pp. 288-293.

Harant, H. et al., "Two-Dimensional Electrophoresis as a Tool for Control of Quality and Consistency in Production Systems Using Animal Cells"; 1992; Cytotechnology; vol. 8; pp. 119-127.

Harrison, S. et al., "The Manufacturing Process for Recombinant Factor IX"; Apr. 1998; Seminars in Hematology; vol. 35(2), Suppl. 2; pp. 4-10.

Hassell, T. et al., "Stability of Production of Recombinant Antibodies from Glutamine Synthetase Amplified CHO and NS0 Cell Lines"; 1992; Animal Cell Technology: Developments, Processes and Products, 11th ESACT Meeting; pp. 42-47.

Hayter et al., "Glucose-Limited Chemostat Culture of Chinese Hamster Ovary Cells Producing Recombinant Human Interferon-γ," Biotechnology and Bioengineering, vol. 39, pp. 327-335 (1992).

Heidemann, R. et al., "The Use of Peptones as Medium Additives for High-Density Perfusion Cultures of Animal Cells"; Poster Presented at the 16th ESACT Meeting, Apr. 25-29, 199, Lugano, Switzerland; 3 pages.

Holtta et al., "Polyamine dependence of Chinese hamster ovary cells in serum-free culture is due to deficient Arginase activity," Biochem Biophys Acta, 721(4):321-327 (1982).

Hsieh, C.M. et al., "The Effect of Soy Protein Hydrolyzates on Fermentation by *Lactobacillus amylovorus*"; 1999; Process Biochemistry; vol. 34; pp. 173-179.

Igarashi et al., "Polyamines: Mysterious Modulators of Cellular Functions," Biochem Biophys Res Commun, vol. 271, No. 3, pp. 559-564 (2000).

Inoue, Y. et al., "Production of Recombinant Human Monoclonal Antibody Using ras-Amplified BHK-21 Cells in a Protein-free Medium"; 1996; Biosci. Biotech. Biochem.; vol. 60(5); pp. 811-817.

International Search Report from PCT/EP2007/000027, dated Sep. 3, 2001 (1 page).

Ito, Y. et al., "Protein-Free Cell Culture on an Artificial Substrate with Covalently Immobilized Insulin"; 1996; Proc. Natl. Acad. Sci. USA; vol. 93; pp. 3598-3601.

Jan, D.C-H. et al., "Peptone a Low-Cost Growth-Promoting Nutrient for Intensive Animal Cell Culture"; Cytotechnology; vol. 16; pp. 17-26.

Jin, B.R. et al., "Production Kinetics and Stability of a Transfectoma Cell Line Secreting Murine/Human Chimeric Antibody"; 1993; Mol. Cells; vol. 3; pp. 233-237.

Kadouri, A. et al., "Dynamic Changes in Cytokine Secretion by Stromal Cells During Prolonged Maintenance Under Protein-Free Conditions"; 1992: International Journal of Cell Cloning; vol. 10; pp. 299-308.

Katinger, H. et al., "Long-Term Stability of Continuously Perfused Animal Cells Immobolized on Novel Macroporous Microcarriers"; 1996; Adv. Molecul. Cell Biol.; vol. 15A; pp. 193-207.

Katsuta, H. and Takaoka, T., "Amino Acid Requirements of a Substrain of StrainL Cells (Mouse Fibroblasts) in Protein-Free Chemically Defined Synthetic Media"; 1960; Japan J. Exp. Med.; vol. 30; pp. 235-259.

Katsuta, H. et al., "Effects of Polyamines on the Proliferation of Mammalian Cells in Tissue Culture"; 1975; The Japanese Journal of Experimental Medicine; vol. 45; No. 5; pp. 345-354.

Kaufman, K. et al., "Effect of von Willebrand Factor Coexpression on the Synthesis and Secretion of Factor VIII in Chinese Hamster Ovary Cells"; 1989; Molecul. Cellul. Biol.; vol. 9(3); pp. 1233-1242.

Keay, L., "Autoclavable Low Cost Serum-Free Cell Culture Media: the Growth of Established Cell Lines and Production of Viruses"; 1976; Biotechnology and Bioengineering; vol. XVIII; pp. 363-382.

Keay, L., "Autoclavable Low Cost Serum-Free Culture Media, The Growth of L Cells and BHK Cells on Peptones"; 1975; Biotechnology and Bioengineering; vol. XVII; pp. 745-764.

Keen, M.J. and Rapson, N.T., "Development of a Serum-Free Culture Medium for the Large Scale Production of Recombinant Protein From a Chinese Hamster Ovary Cell Line"; 1995; Cytotechnology; vol. 17; pp. 153-163.

Kerry Ingredients (UK) Limited Opposition Brief to European Patent No. 1220893, dated Mar. 21, 2007.

Kim, S.J. et al., "Characterization of Chimeric Antibody Producing CHO Cells in the Course of Dihydrofolate Reductase-Mediated Gene Amplification and Their Stability in the Absence of Selective Pressure"; Apr. 5, 1998; Biotechnology and Bioengineering; vol. 58(1); pp. 73-84.

Kim, N.S. et al., "Clonal Variability Within Dihydrofolate Reductase-Mediated Gene Amplified Chinese Hamster Ovary Cells: Stability in the Absence of Selective Pressure"; Dec. 20, 1998; Biotechnology and Bioengineering; vol. 60(6); pp. 679-688.

Kim et al., "Effects of supplementation of various medium components on Chinese hamster ovary cell cultures producing recombinant antibody," Cytotechnology, 47 : 37-49 (2005).

Kim et al., "Development of a Serum-Free Mediumfor the Production of Humanized Antibody from Chinese Hamster Ovary Cells Using a Statistical Design," In Vitro Cell Dev Biol, vol. 34, pp. 757-761 (1998).

(56) References Cited

OTHER PUBLICATIONS

Kwon, M.S. et al., "Use of Plant-Derived Protein Hydrolysates for Enhancing Growth of *Bombyx mori* (silkworm) Insect Cells in Suspension Culture"; 2005; Biotechnology and Applied Biochemistry; vol. 42, No. 1; pp. 1-7.
Lee, K.H. et al., "Deregulated Expression of Cloned Transcription Factor E2F-1 in Chinese Hamster Ovary Cells Shifts Protein Patterns and Activates Growth in Protein-Free Medium"; 1996; Biotechnol. Bioeng.; vol. 50; pp. 273-279.
Lee et al., "The effects of various hormones and growth factors on the growth of human insulin-producing cell line in serum-free medium," Experimental and Molecular Medicine, 29(4): 209-216 (1997).
Luchette, C. et al., "Isolation and Characterization of a CHO Cell Line Express rhFSH in Low Protein and Protein-Free Media"; 1997; Animal Cell Technology; pp. 669-674.
Maxygen, Inc. Opposition Brief to European Patent No. 1200561, dated Mar. 14, 2007.
Maxygen, Inc. Opposition Brief to European Patent No. 1220893, dated Mar. 20, 2007.
Merck Serono International S.A. Opposition Brief to European Patent No. 1200561, dated Mar. 12, 2007.
Merck Serono International S.A. Opposition Brief to European Patent No. 1220893, dated Mar. 20, 2007.
Merten, O.-W. et al., "Production of Influenza Virus in Serum-Free Mammalian Cell Cultures"; 1999; Dev. Biol. Stand.; vol. 98; pp. 23-37.
Merten, O.-W. et al., "The New Medium MDSS2N, Free of Any Animal Protein Supports Cell Growth and Production of Various Viruses"; 1999; Cytotechnology; vol. 30; pp. 191-201.
Merten, O.-W., "Safety Issues of Animal Products Used in Serum-Free Media"; 1999; Dev. Biol. Stand.; vol. 99; pp. 167-180.
Miao, jinmin et al., "The influences of Polymine on Protein Metabolism," 1991, Foreign Medical Sciences, vol. 13, No. 1, pp. 33-36.
Miyaji, H. et al., "Efficient Expression of Human Beta-interferon in Namalwa KJM-1 Cells Adapted to Serum-free Medium by dhfr Gene Coamplification Method"; 1990; Cytotechnology; vol. 4; pp. 173-180.
Miyaji, H. et al., "Expression of Human Beta-interferon in Namalwa KJM-1 Which Was Adapted to Serum-free Medium"; 1990; Cytotechnology; vol. 37; pp. 133-140.
Miyazaki et al., "Spermine enhances IgM productivity of human-human hybridoma HB4C5 cells and human peripheral blood lymphocytes," Cytotechnology, vol. 26, pp. 111-118 (1998).
Morris, D.R. et al., "Isolation of Conditionally Putrescine-Deficient Mutants of *Escherichia coli*"; 1970; J. Bacteriol. vol. 101; pp. 731-737.
Motz, M. et al., "Expression of the Epstein-Barr Virus Major Membrane Proteins in Chinese Hamster Ovary Cells"; 1986; Gene; vol. 44(2-3); pp. 353-359; Abstract, 1 page.
Mutsksmi et al., "Hormonal control of human colon carcinoma cell growth in serum-free medium," PNAS, 77(6):3464-3468 (1980).
Murhammer, D.W. and Gooche, C.F., "Structural Features of Nonionic Polyglycol Polymer Molecules Responsible for the Protective Effect in Sparged Animal Cell Bioreactors"; 1990; Biotechnol. Prog.; vol. 6; pp. 142-146.
Nilsson, K. et al., "Microcarrier Culture of Recombinant Chinese Hamster Ovary Cells for Production of Human Immune Interferon and Human Tissue-Type Plasminogen Activator"; 1988; Appl. Microbiol. Biotechnol.; vol. 27; pp. 366-371.
Novartis AG Opposition Brief to European Patent No. 1200561, dated Mar. 14, 2007.
Novartis AG Opposition Brief to European Patent No. 1220893, dated Mar. 21, 2007.
Novo Nordisk A/S Opposition Brief to European Patent No. 1200561, dated Mar. 14, 2007.
Novo Nordisk A/S Opposition Brief to European Patent No. 1220893, dated Mar. 21, 2007.
N.V. Organon Opposition Brief to European Patent No. 1200561, dated Mar. 14, 2007.

Nyberg, G.B. et al., "Metabolism of Peptide Amino Acids by Chinese Hamster Ovary Cells Grown in a Complex Medium"; Feb. 5, 1999; Biotechnology and Bioengineering; vol. 62(3); pp. 324-335.
Ochiai, M. et al., "Endotoxin Content in *Haemophilus influenzae* Type b Vaccine"; 2004; Jpn. J. Infect. Dis.; vol. 57; pp. 58-59.
Ogata, M. et al., "High-Level Expression of Recombinant Human Soluble Thrombomodulin In Serum-Free Medium by CHO-K1 Cells"; 1993; Appl. Mircobiol. Biotechnol.; vol. 38; pp. 520-525.
Oleksowicz et al., "Deficient Activity of von Willebrand's Factor-cleaving Protease in Patients with Disseminated Malignancies," Cancer Research, vol. 59, pp. 2244-2250 (1999).
Opposition Against EP 2522717B1, filed on Dec. 30, 2014, by CSL Behring GmbH, 14 pages.
Opposition Against EP 2522717B1, filed on Jan. 5, 2015 by Dr. Ursula Sprenzel, 43 pages.
Organische Chemie II, Breitmaier E. and Jung G. (ed.), Georg Thieme Verlag Stuttgart, Germany, p. 39 (1983).
Page from the Quest International Technical Manual on Hydrolysates, 1988.
Pak, S.C.O. et al., "Super-CHO—A Cell Line Capable of Autocrine Growth Under Fully Defined Protein-Free Conditions"; 1996; Cytotechnology; vol. 22; pp. 139-146.
Pastorian et al., "Tolerance to Putrescine Toxicity in Chinese Hamster Ovary Cells is Associated with Altered Uptake and Export," Exp. Cell Res., 231:284-295 (1997).
Paterson, T. et al., "Approaches to Maximizing Stable Expression of α1-Antitrypsin in Transformed CHO Cells"; 1994; Appl. Microbiol. Biotechnol.; vol. 40; pp. 691-698.
Pu, H. et al., "Rapid Establishment of High-Producing Cell Lines Using Dicistronic Vectors with Glutamine Synthetase as the Selection Marker"; 1998; Molecular Biotechnology; vol. 10; pp. 17-25.
Qi, Y.M. et al., "Evaluation of a Simple Protein Free Medium That Supports High Levels of Monoclonal Antibody Production"; 1996; Cytotechnology; vol. 21; pp. 95-109.
Quest International; "Protein Derived Peptide Mixtures can Effectively Replace Serum, Glutamine and Other Free Amino Acids in Cell Culture Media"; Nov. 1998; Research Disclosure; pp. 1474-1476.
Quest International; Bioproducts Group HY-SOY®, Product Information, 1995, 1 page.
Quest International; Bioproducts Group HY-SOY®, Product Information, 1998, 2 pages.
Quest International: Product Information; www.sheffield-products.com; accessed on Nov. 18, 2003; 14 pages.
Rasmussen, B. et al., "Isolation, Characterization and Recombinant Protein Expression in Veggie-CHO: A Serum-Free CHO Host Cell Line"; 1998; Cytotechnology; vol. 28; pp. 31-42.
Reiter, M. et al., "Flow Cytometry and Two-Dimensional Electrophoresis (2-DE) for System Evaluation of Long Term Continuous Perused Animal Cell Cultures in Macroporous Beads"; 1992; Cytotechnology; vol. 9; pp. 247-253.
Renner, W.A. et al., "Recombinant Cyclin E Expression Activates Proliferation andObvates Surface Attachment of Chinese Hamster Ovary (CHO) Cells in Protein-Free Medium"; Aug. 1995; Biotechnology and Bioengineering; vol. 47; pp. 476-482.
Rompp Chemie Lexikon, 9 ed, Falbe J. and Regitz M. (ed.), Georg Thieme Verlag Stuttgart, Germany, p. 3268-3269 (1995).
Ryll, T. et al., "Production of Recombinant Human Interleukin-2 with BHK Cells in a Hollow Fibre and a Stirred Tank Reactor with Protein-Free Medium"; 1990; Journal of Biotechnology; vol. 14; pp. 377-392.
SAFC Biosciences™; Dulbecco's Modified Eagle's Medium/Ham's Nutrient Mixture F12 Product Information, 2006, 2 pages.
SAFC Biosciences™; RPMI 1640 Medium Modified Product Information, 2006, 2 pages.
Scharfenberg, K. and Wagner, R., "A Reliable Strategy for the Achievement of Cell Lines Growing in Protein-Free Medium"; 1995; Animal Cell Technology: Developments towards the 21st Century; pp. 619-623.
Schlaeger, E.J., "The Protein Hydrolystate, Primatone RL, is a Cost-Effective Multiple Growth Promoter of Mammalian Cell Cul-

(56) References Cited

OTHER PUBLICATIONS ture in Serum-Containing and Serum-Free Media and Displays Anti-apoptosis Properties"; 1996; Journal of Immunological Methods; vol. 194; pp. 191-199.
Schlokat, U. et al., "Herstellung and Charakterisierung von rekombinantem vonWillebrand-Faktor zur Therapeutischen Anwendyng"; 1995; 26th Hämophilie-Symposium Hamburg; pp. 147-158.
Schlokat, U. et al., "Production of Highly Homogeneous and Structurally Intact Recombinant von Willebrand Factor Multimers by Furin-Mediated Propeptide Removal in vitro"; 1996; Biotechnol. Appl. Biochem.; vol. 24; pp. 257-267.
Schneider, Y-J, "Optimisation of Hybridoma Cell Growth and Monoclonal Antibody Secretion in a Chemically Defined, Serum- and Protein-Free Culture Medium"; 1989; Journal of Immunological Methods; vol. 116; pp. 65-77.
Scientific Discussion for the approval of BeneFIX issued by the EMA, updated until Sep. 1, 2000.
Sigma®; Biochemicals Organic Compounds Diagnostic Reagents Catalogue, 1995, 6 pages.
Sigma-Aldrich; DME/Nutrient Mixture F12 Ham Product Information, 8 pages.
Sigma-Aldrich; IPL-41 Insect Medium Product Information, 1 page.
Sigma-Aldrich; Minimum Essential Medium Eagle (MEM), Product Information, 6 pages.
Sigma-Aldrich; Minimum Essential Medium Eagle, Joklik Modification, Specification Sheet, 1 page.
Sigma-Aldrich; P1265 N-Z Soy Peptone Product Detail, 1 page.
Sigma-Aldrich; P6463 Peptone Hy-Soy® T Product Detail, 1 page.
Sigma-Aldrich Co. Opposition Brief to European Patent No. 1220893, dated Mar. 21, 2007.
Sinacore, M.S. et al., "Cho DUKX Cell Lineages Preadapted to Growth in Serum-Free Suspension Culture Enable Rapid Development of Cell Culture Processes for the Manufacture of Recombinant Proteins"; 1996; Biotechnol. Bioeng.; vol. 52; pp. 518-528.
Stoll, T.S. et al. "Effects of Culture Conditions on the Production and Quality of Monoclonal IgA"; Aug. 15, 1997; Enzyme and Microbial Technology; vol. 21; pp. 203-211.
Sunstrom, N-A. et al., "Recombinant Insulin=like Growth Factor-I (IGF-I) Production in Super-CHO Results in the Expression of IGF-I Receptor and IGF Binding Protein 3"; 1998; Cytotechnology; vol. 28; pp. 91-99.
Takashi, M. et al., "Production of Murine Monoclonal Antibodies in Protein Free Medium"; 1997; Animal Cell Technology: Basic & Applied Aspects; vol. 8; pp. 167-171.
Taylor, W.G. et al., "Studies on a Serum Substitute for Mammalian Cells in Culture. I. Biological Efficacy of Whole and Fractionated Peptone Dialysate (36086)"; 1972; Proc. Soc. Exp. Biol. Med.; vol. 139; pp. 96-99.
Tecce, M.F. and Terrana B., "High Yield and High-Degree Purification of Human α-Fetoprotein Produced by Adaptation of the Human Hepatoma Cell Line HEP G2 in a Serum-Free Medium"; 1988; Analytical Biochemistry; vol. 169; pp. 306-311.
Teige, M. et al., "Problems with Serum-Free Production of Antithrombin III Regarding Proteolytic Activity and Product Quality"; 1994; Journal of Biotechnology; vol. 34; pp. 101-105.
Third Party Observation, dated Oct. 28, 2014, filed for EP Application No. 1974014, 7 pages.
Werner, R.G. et al., "Safety and Economic Aspects of Continuous Mammalian Cell Culture"; 1992; Journal of Biotechnology; vol. 22; pp. 51-68.

Wilson et al., "The effects of various nutritional supplements on the growth, migration and differentiation of *Xenopus laevis* neural crest cells in vitro," In Vitro Cell. Dev. Biol., 23(5):323-331 (1987).
Wyeth Opposition Brief to European Patent No. 1200561, dated Mar. 14, 2007.
Yamauchi, T. et al., "Production of Human Antithrombin-III in a Serum-Free Culture of CHO Cells"; 1992; Biosci. Biotech. Biochem.; vol. 56(4); pp. 600-604.
Yin, Z. et al., "Sensitivity of 3T3 Cells to Low Serum Concentration and the Association Problems of Serum Withdrawal"; 1994; Cell Biology International; vol. 18(1); pp. 39-46.
Zang, M. et al., "Production of Recombinant Proteins in Chinese Hamster Ovary Cells Using a Protein-Free Cell Culture Medium"; 1995; Biotechnology; vol. 13; pp. 389-392.
GIBCO™ Invitrogen Corporation, "Technologies for Monoclonal Antibody Production," 2001, pp. 1-8.
Nolasco et al., "Hemolytic uremic syndrome-associated Shiga toxins promote endothelial-cell secretion and impair ADAMTS13 cleavage of unusually large von Willebrand factor multimers," Blood, 2005, 106: 4199-4209.
Opposition filed by CSL Behring GmbH, dated Mar. 22, 2016, against European Patent No. 2 522 717, 5 pages.
Opposition filed by Dr. Ursula Sprenzel, dated Mar. 24, 2016, against European Patent No. 2 522 717, 12 pages.
"Production of Biologicals from Animal Cells in Culture," European Society for Animal Cell Technology, The 10th Meeting, 1991, 18 pages.
Sugahara et al., "Effects of polyamines on proliferation and IgM productivity of human-human hybridoma, HB4C5 cells," Cytotechnology (2008) 57:115-122.
Wikipedia, "Tissue plasminogen activator," [retrieved from the Internet on Mar. 23, 2016] URL: <https://en.wikipedia.org/wiki/Tissue_plasminogen_activator>, 35 pages.
Written statement of grounds of appeal from Opponent 1, CSL Behring GmbH, in corresponding European Patent No. 2522717 B1, Oct. 13, 2016.
Raina et al., "Roles of polyamines in the replication of animal viruses," Med. Biol. Dec. 1981, vol. 59, pp. 428-432, abstract.
EMEA Note for Guidance on Quality of Biotechnological Products: Analysis of the Expression Construct in Cell Lines Used for Production of r-DNA Derived Protein Products (CPMP/ICH/139/95) July 1996, 5 pages.
EMEA Note for Guidance on Quality of Biotechnological Products: Derivation and Characterisation of Cell Substrates Used for Production of Biotechnological/Biological Products (CPMP/ICH/294/95) Mar. 1998, 13 pages.
Extracts from dictionaries defining the term "oligopeptide." [retrieved from the Internet Dec. 23, 2014], 8 pages.
Opponent 1, CSL Behring GmbH, reply to Baxalta's written statement of grounds of appeal in corresponding European Patent No. 2522717, dated Feb. 28, 2017, 34 pages.
Opponent II, Dr. Ursula Sprenzel, response to Baxalta's statement of grounds of appeal in corresponding European Patent No. 2522717, dated Feb. 28, 2017, 29 pages.
Davarani et al., "Choosing a Host Cell for Active Recombinant Factor VIII Production Using Vaccinia Virus," Bio/Technology, vol. 5, Apr. 1987, pp. 389-392.
Primrose et al., "Principles of Gene Manipulation, Sixth Edition, Chapter 10, Gene transfer to animal cells," pp. 174-199, Blackwell Science 2001.
Screenshot of https:thermofisher.com/order/catalog/product/ME080160L1, 1 pages, date unknown.
Dictionary of Biochemistry, 1984, First Edition, Tokyo Kagaku Dojin, 4 pages.

* cited by examiner

Figure 2

|  | QP [U/L/D] | qp [mU/10E06 cells/ day] | μ [ d$^{-1}$ ] |
|---|---|---|---|
| BAV-Medium without supplement | 271 | 236 | 0.37 |
| BAV-Medium + Putrescine.2HCl (2 mg/L) | 870 | 671 | 0.41 |
| BAV-Medium + Putrescine.2HCl (2 mg/L) + Fe(II) ad 2.3 x concentration + Cu (II) ad 2.0 x concentration | 1393 | 958 | 0.59 |
| BAV-Medium + Putrescine.2HCl (2 mg/L) + Fe(II) ad 2.3 x concentration + Cu (II) ad 12.5 x concentration | 2685 | 1744 | 0.63 |
| BAV-Medium + Putrescine.2HCl (2 mg/L) + Fe(II) ad 2.3 x concentration + Cu (II) ad 12.5 x concentration With increased cell density | 3107 | 1756 | 0.63 |

Figure 3

|  | qp absolute [mU/10E06 cells/ day] | qp relative [ % ] | µ absolute [ d-1 ] | µ relative [ % ] |
|---|---|---|---|---|
| BAV medium without additional biogenic amine | 172 | 100 | 0.19 | 100 |
| Putrescine.2HCl (2 mg/L) | 697 | 405 | 0.34 | 179 |
| Ornithine.HCl (2 mg/L) | 457 | 266 | 0.34 | 179 |
| Ornithine.HCl (10 mg/L) | 587 | 341 | 0.37 | 195 |
| Putrescine.2HCl (2 mg/L) +Ornithine.HCl (2 mg/L) | 806 | 467 | 0.36 | 189 |
| Putrescine.2HCl (2 mg/L) +Ornithine.HCl (10 mg/L) | 1050 | 610 | 0.39 | 205 |

Figure 4

| | qp absolute [mU/10E06 cells/ day] | qp relative [ % ] | μ absolute [ d-1 ] | μ relative [ % ] |
|---|---|---|---|---|
| Putrescine.2HCl (2 mg/L) | 2303 | 100 | 0.61 | 100 |
| Spermine.4HCl (0.4 mg/L) | 1331 | 58 | 0.59 | 97 |
| Spermine.4HCl (2 mg/L) | 2639 | 115 | 0.60 | 98 |
| Spermine.4HCl (10 mg/L) | 2651 | 115 | 0.59 | 97 |

Figure 5

| | qp absolute [mU/10E06 cells/day] | qp relative [%] | µ absolute [d-1] | µ relative [%] |
|---|---|---|---|---|
| BAV medium standard Ethanolamine (1.53 mg/L) Stand. conc.=neg. control | 172 | 100 | 0.19 | 100 |
| Ethanolamine (ad 3.83 mg/L) | 188 | 109 | 0.23 | 118 |
| Ethanolamine (ad 15.3 mg/L) | 183 | 106 | 0.22 | 118 |
| Ethanolamine (ad 38.3 mg/L) | 171 | 100 | 0.23 | 125 |
| Putrescine.2HCl (2 mg/L) +Ethanolamine (ad 3.83 mg/L) | 545 | 317 | 0.36 | 193 |
| Putrescine.2HCl (2 mg/L) +Ethanolamine (ad 15.3 mg/L) | 609 | 354 | 0.32 | 173 |
| Putrescine.2HCl (2 mg/L) +Ethanolamine (ad 38.3 mg/L) | 553 | 322 | 0.32 | 172 |

OLIGOPEPTIDE-FREE CELL CULTURE MEDIA

CROSS-REFERENCE TO RELATED APPLICATIONS

This application is a continuation of U.S. patent application Ser. No. 13/035,696 filed Feb. 25, 2011, which is a continuation of U.S. patent application Ser. No. 11/649,694 filed Jan. 3, 2007, which claims benefit of U.S. provisional application Ser. No. 60/756,419 filed Jan. 4, 2006, which applications are herein incorporated by reference.

FIELD OF THE INVENTION

The present invention relates to oligopeptide-free cell culture media comprising at least 0.5 mg/L of a polyamine and to methods for cultivating cells in said oligopeptide-free cell culture media comprising at least 0.5 mg/L of a polyamine. The invention also relates to methods for expressing at least one protein in a medium comprising at least 0.5 mg/L of a polyamine and to methods for producing at least one virus in a medium comprising at least 0.5 mg/L of a polyamine.

BACKGROUND OF THE INVENTION

For cultivation of cells, particularly eukaryotic cells, and more specifically mammalian cells, there is a constant need to use special culture media providing nutrient substances that are required for efficient growth of cells and for the production of biological products, especially biopharmaceuticals, such as, for example, recombinant proteins, antibodies, viruses, viral antigens, and virus-like particles. For the efficient production of said biological products, it is important to achieve an optimal cell density as well as an increase of the protein expression itself in order to obtain maximal product yield.

Cell culture media formulations have been supplemented with a range of additives, including undefined components like fetal calf serum (FCS), several animal derived proteins and/or protein hydrolysates of bovine origin as well as protein hydrolysates derived from plants or yeast.

In general, serum or serum-derived substances, such as, e.g., albumin, transferrin or insulin, may comprise unwanted agents that can contaminate the cell cultures and the biological products obtained thereof. Furthermore, human serum derived additives have to be tested for all known viruses, including hepatitis viruses and HIV which can be transmitted via serum. Moreover, bovine serum and products derived thereof bear the risk of BSE contamination. In addition, all serum-derived products can be contaminated by unknown substances. When using serum or protein additives derived from human or animal sources in cell culture, there are numerous problems (e.g., the varying quality in composition of different batches and the risk of contamination with mycoplasma, viruses or BSE), particularly if the cells are used in the manufacture of drugs or vaccines for human administration.

Therefore, many attempts have been made to provide efficient host systems and cultivation conditions, which do not require serum or other animal protein compounds.

Such serum-free media have been developed on the basis of protein extracts derived from plants or yeast. For example, soy hydrolysates are known to be useful for fermentation processes and can enhance the growth of many fastidious organisms, yeasts and fungi. WO 96/26266 describes that papaic digests of soy meal are a source of carbohydrate and nitrogen and many of the components can be used in tissue culture. Franek et al. (Biotechnology Progress (2000) 16, 688-692) describe growth and productivity promoting effects of defined soy and wheat hydrolysate peptide fractions.

WO 96/15231 discloses a serum-free medium composed of a synthetic minimal essential medium and a yeast extract for the propagation of vertebrate cells and a virus production process. A medium formulation composed of a basal cell culture medium comprising a rice peptide and an extract of yeast and an enzymatic digest thereof, and/or a plant lipid for growth of animal cells is disclosed in WO 98/15614. A medium comprising purified soy hydrolysate for the cultivation of recombinant cells is disclosed in WO 01/23527. WO 00/03000 discloses a medium that comprises a soy hydrolysate and a yeast extract, but also requires the presence of recombinant forms of animal proteins, such as growth factors.

EP-A-0 481 791 describes a biochemically defined culture medium for culturing engineered CHO cells, which is free from protein, lipid and carbohydrate isolated from an animal source, further comprising a recombinant insulin or insulin analogue, 1% to 0.025% w/v papain digested soy peptone and putrescine. WO 98/08934 describes a serum-free eukaryotic cell culture comprising hydrolyzed soy peptides (1-1000 mg/L), 0.01 to 1 mg/L putrescine and a variety of animal-derived components, including albumin, fetuin, various hormones and other proteins. In this context, it should be noted that putrescine is also known to be comprised in standard media like DMEM/Ham's F12 in a concentration of 0.08 mg/L.

The plant and/or yeast hydrolysates, however, are undefined mixtures of oligopeptides and other unknown components and contaminants. Moreover, the quality of commercially available lots of hydrolysates varies extremely. As a result, there are large variations in the production of recombinant proteins or viral products (a variation of up to a factor of 3) as a function of the lots of hydrolysates used ("lot-to-lot variation"). This drawback affects the proliferation of the cells as well as the protein expression of each cell.

In summary, the media known in the state of the art are supplemented with proteins or peptide extracts derived from animals, plants, or yeast; or with recombinant versions of proteins, such as, for example, insulin, insulin like growth factor or other growth factors.

Therefore, there is a need for a cell culture medium which is free of animal, herbal, and fungal proteins and/or oligopeptides in order to overcome the above-mentioned problems. Furthermore, a current need exists to increase the yield of expressed recombinant proteins or any other expression product, and to provide an optimal cell culture medium for the production of biological products, such as those used as pharmaceuticals or vaccines in humans.

SUMMARY OF THE INVENTION

It is an object of the present invention to provide oligopeptide-free cell culture media. A further object of the present invention is to provide methods for cultivating cells in said media as well as methods for efficient expression of recombinant proteins and/or methods for the efficient production of viruses.

It is another object of the present invention to eliminate animal, plant and/or yeast derived hydrolysates and to provide media which do not comprise any added supplementary proteins or oligopeptides.

Surprisingly, the addition of at least 0.5 mg/L of a polyamine to cell culture media provides an advantageous effect not only by promoting cell growth but also by increasing the protein and/or virus expression per cell. Said unexpected advantageous effect can be achieved even in oligopeptide-free media.

Further, the oligopeptide-free medium according to the present invention allows consistent cell growth and increased yield of desired products, particularly of target proteins such as recombinant proteins and/or viruses, independent of the quality or lot variations of any protein hydrolysates. The specific supplementation of cell culture media with a specific concentration of polyamines acts to increase cell growth, cell specific productivity and final cell density.

Therefore, the media according to the present invention are more favorable for recombinant protein expression, virus production and cell growth rate compared to the media known in the art. Furthermore, the oligopeptide-free medium according to the present invention obviates the addition of protein hydrolysate to the cell culture medium.

BRIEF DESCRIPTION OF THE DRAWINGS

FIG. 2 shows a table which compares the effect of the addition of putrescine optionally in combination with the additional supplementation with Fe (II) and Cu (II) on the volumetric and cell specific productivity (QP, expressed in [Units per Liter per Day], qp, expressed in [mU per 10E06 cells per day]) and on the specific growth rate p, expressed as specific growth rate per day in $[d^{-1}]$ of GD8/6 cells cultivated in BAV-medium.

FIG. 3 shows a table which compares the effect of putrescine and/or ornithine on the specific growth rate (μ absolute, μ relative) and the cell specific productivity (qp absolute, expressed in [mU per 10E06 cells per day], qp relative, expressed in %) of GD8/6 cells cultivated in BAV-medium.

FIG. 4 shows a table which compares the effect of putrescine and spermine on the specific growth rate (μ absolute, μ relative) and the cell specific productivity (qp absolute, qp relative) of GD8/6 cells cultivated in BAV-medium.

FIG. 5 shows a table which compares the effect of putrescine and ethanolamine on the specific growth (μ absolute, μ relative) and the cell specific productivity (qp absolute, qp relative) of GD8/6 cells cultivated in BAV-medium.

DETAILED DESCRIPTION OF THE INVENTION

Figure 1:
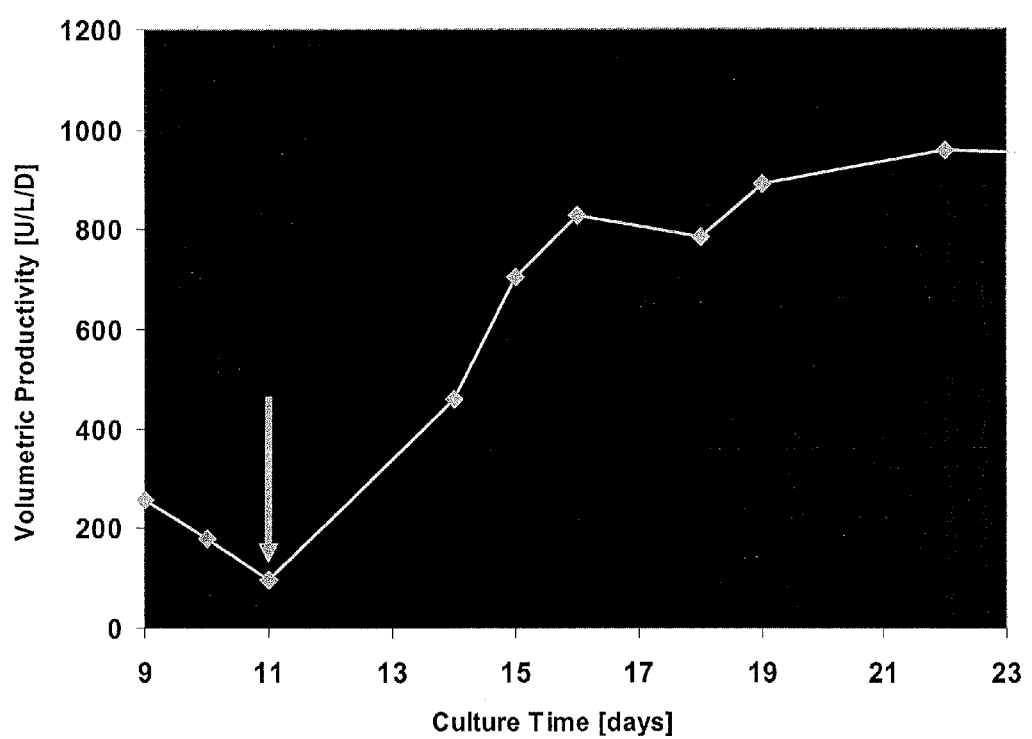
FIG. 1 shows a graph which describes the effect of the addition of 2.0 mg/L putrescine.2HCl on the volumetric FVIII-CoA productivity, expressed in [Units per Liter per Day], of GD8/6 cells cultivated in BAV-medium over the culture time, expressed in [days]. Arrow=Day 11: Addition of Putrescine.2HCl (2.0 mg/l)

One aspect of the invention relates to an oligopeptide-free cell culture medium comprising at least 0.5 mg/L of a polyamine.

Unless stated differently, concentration values indicated throughout this document refer to the free base form of the component(s).

The term "polyamine" refers to any of the group of biogenic polyamines, which are organic polycations derived from aromatic or cationic amino acids. Polyamines are composed of carbon, nitrogen, and hydrogen and comprise two or more amino groups. Polyamines have one or more positive charges and a hydrophobic skeleton. The term encompasses, for example, molecules selected from the group consisting of cadaverine, putrescine, spermidine, spermine, agmatine, ornithine, and combinations thereof. In one embodiment of the invention, the oligopeptide-free culture medium comprises ornithine, or putrescine, or spermine, or combinations thereof.

In another embodiment of the oligopeptide-free cell culture medium according to the invention the polyamine originates from a source other than a protein hydrolysate. In one embodiment, the polyamine is synthetically produced.

In one embodiment of the invention, the polyamine concentration is at least about 0.5 mg/L, in another embodiment at least about 1 mg/L, in a further embodiment at least about 2 mg/L, in still another embodiment at least 5 mg/L, in yet another embodiment at least 8 mg/L, and in a further embodiment at least 10 mg/L.

In one embodiment of the invention, the polyamine concentration ranges from about 0.5 mg/L to about 30 mg/L, in another embodiment from about 0.5 mg/L to about 20 mg/L, in a further embodiment from about 1.0 mg/L to about 20 mg/L, in a further embodiment from about 2.0 mg/L to about 20 mg/L, in a further embodiment from about 2 mg/L to about 10 mg/L, in an alternative embodiment from about 2 mg/L to about 8 mg/L, and in a further embodiment from about 2 mg/L to about 5 mg/L in the medium.

The concentrations indicated above are the respective concentrations of pure polyamine. If a polyamine derivative or a polyamine comprising compound is used, the concentration of the polyamine-group is in the above specified ranges. For example, 2 mg/L Putrescine.2HCl is equivalent to a Putrescine concentration of about 1.095 mg/L (without .2HCl).

The term "oligopeptide-free cell culture medium" according to the invention refers to a protein-free medium that does not comprise oligopeptides, such as, e.g., oligopeptides derived from a protein hydrolysate. In one embodiment, the medium does not comprise oligopeptides having twenty or more amino acids. In one embodiment of the present invention, the medium does not comprise oligopeptides having fifteen or more amino acids. In another embodiment of the invention, the medium does not comprise oligopeptides having ten or more amino acids. In one embodiment the medium does not comprise oligopeptides having seven or more amino acids, in another embodiment it does not comprise oligopeptides having five or more amino acids, in still another embodiment it does not comprise oligopeptides having three or more amino acids. According to a further embodiment of the present invention, the medium does not comprise oligopeptides having two or more amino acids.

The medium according to the invention may optionally comprise glutathione and/or at least one stable form of glutamine, such as, e.g., L-alanyl-L-glutamine. The term "glutathione" as used herein describes a tripeptide composed of the amino acids glutamate, cysteine and glycine including the oxidized form of glutathione, i.e. glutathione disulfide, a glutathione dimer formed by a disulfide bond between the cysteine sulfhydryl side chains during the course of being oxidized.

In an embodiment of the present invention, the oligopeptide-free cell culture medium does not comprise oligopeptides having three or more amino acids, but may optionally comprise glutathione.

In another embodiment, the oligopeptide-free cell culture medium does not comprise oligopeptides having two or more amino acids, but may optionally comprise glutathione and/or at least one stable form of glutamine.

Typical proteins and/or oligopeptides that are avoided in the media according to the invention are those found in serum and serum-derived substances, such as, e.g., albumin, transferrin, insulin or other growth factors as well as recombinant forms thereof, or oligopeptides from plant or yeast hydrolysates or ultrafiltered forms thereof.

The oligopeptide-free culture medium according to the invention may be based on any basal medium, such as DMEM, Ham's F12, Medium 199, McCoy, or RPMI, generally known to a person skilled in the art. The basal medium may comprise a number of ingredients, including amino acids, vitamins, organic and inorganic salts, and sources of carbohydrate, each ingredient being present in an amount which supports the cultivation of a cell, said amounts being generally known to a person skilled in the art. The medium may comprise auxiliary substances, such as buffer substances, e.g., sodium bicarbonate, antioxidants, stabilisers to counteract mechanical stress, or protease inhibitors. If required, a non-ionic surfactant such as copolymers and/or mixtures of polyethylene glycols and polypropylene glycols (e.g., Pluronic F68®, SERVA) can be added.

In an embodiment of the culture medium according to the present invention the polyamine controls DNA- and RNA-synthesis, and/or cell proliferation, and/or cell differentiation, and/or membrane stabilization, and/or antioxidative DNA-protection.

In one embodiment, the addition of at least 0.5 mg/L of a polyamine to an oligopeptide-free cell culture medium increases the protein and/or virus expression in the cultured cells. In another embodiment, the protein expression or virus titer in the cultured cells can be increased by at least 50% by the addition of at least 0.5 mg/L of a polyamine to an oligopeptide-free cell culture medium. In still another embodiment said increase is at least 60%. In yet another embodiment the cell specific productivity is increased at least two-fold by the addition of at least 0.5 mg/L of a polyamine to an oligopeptide-free cell culture medium; in another embodiment the cell specific productivity is increased at least three-fold. In still another embodiment, the addition of at least 0.5 mg/L of a polyamine results in an increase in protein expression and/or virus titer to at least 400%; in a further embodiment to at least 500%; in another embodiment to at least 600%; in a further embodiment to at least 700%.

In one embodiment the specific growth rate of the cultured cells can be increased by the addition of at least 0.5 mg/L of a polyamine to an oligopeptide-free cell culture medium. In a further embodiment, said specific growth rate can be increased by 10%. In still another embodiment, said specific growth rate can be increased by 20%. In yet another embodiment, said specific growth rate can be increased by 50%. In a further embodiment, said specific growth rate can be increased by 70%. In another embodiment, said specific growth rate can be increased by 80%. In still another embodiment, said specific growth rate can be increased by 90%. In yet another embodiment, said specific growth rate can be increased by 100%.

In a further embodiment of the present invention, the medium is chemically defined. The term "chemically defined" as used herein shall mean, that the medium does not comprise any undefined supplements, such as, for example, extracts of animal components, organs, glands, plants, or yeast. Accordingly, each component of a chemically defined medium is accurately defined.

The present invention further relates to a method for cultivating cells, comprising the steps of:
    (a) providing an oligopeptide-free cell culture medium according to the invention, and
    (b) propagating the cells in the medium to form a cell culture.

The present invention is not limited to any type of cells. Examples of cell types include mammalian cells, insect cells, avian cells, bacterial cells, and yeast cells. The cells may be, for example, stem cells or recombinant cells transformed with a vector for recombinant gene expression, or cells transfected with a virus for producing viral products. The cells may also be for example cells producing a protein of interest without recombinant transformation, e.g., a B-cell producing an antibody, which may be transformed into an immortalized status, e.g., by viral infection like Epstein Barr Virus infection. The cells may also be for example primary cells, e.g., chicken embryo cells, or primary cell lines. Useful are cells that are used for in vitro virus production. Specific examples of useful cells include BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, CHO cells, NS-1 cells, MRC-5 cells, WI-38 cells, BHK cells, 293 cells, RK cells, Per.C6 cells and chicken embryo cells.

The cells used according to the present invention may be cultivated, e.g., by a method selected from the group of batch-cultivation, feed-batch-cultivation, perfusion cultivation and chemostate-cultivation, all of which are generally known in the field.

The present invention further relates to a method for expressing at least one protein, such as, e.g., a heterologous or autologous protein or a recombinant protein, comprising the steps of:
    a) providing a culture of cells;
    b) introducing at least one nucleic acid sequence comprising a sequence coding for at least one protein into the cells;
    c) selecting the cells carrying the nucleic acid sequence; and
    d) expressing the protein in the cells in a medium comprising at least 0.5 mg/L of a polyamine.

In one embodiment of the present invention, the medium of step d) is an oligo-peptide-free medium according to the present invention. In a further embodiment of the present invention, the cells of the culture of step a) have been grown in an oligopeptide-free cell culture medium according to the present invention. In another embodiment, steps a) to d) are conducted in an oligopeptide-free cell culture medium according to the invention.

The nucleic acid sequence comprising a sequence coding for at least one protein may be a vector. The vector may be delivered by a virus or may be a plasmid. The nucleic acid sequence coding for the protein may be a specific gene or a biologically functional part thereof. In one embodiment the protein is at least a biologically active part of a blood coagulation factor such as Factor VIII or at least a biologically active part of a protein involved in the production of red blood cells and angiogenesis such as erythropoeitin, or a monoclonal antibody.

In an embodiment, the nucleic acid sequence comprises a sequence coding for at least one protein selected from the group of coagulation factor VII, coagulation factor VIII, coagulation factor IX, vWF, ADAMTS13, and furin.

In an embodiment of the present invention, the nucleic acid further comprises other sequences suitable for a controlled expression of a protein such as promotor sequences, enhancers, TATA boxes, transcription initiation sites, polylinkers, restriction sites, poly-A-sequences, protein processing sequences, selection markers, and the like which are generally known to a person skilled in the art.

In one embodiment of the invention, the cells are selected from the group of CHO cells, 293 cells, and BHK cells.

According to another embodiment of the present invention the following cell lines may be transformed with a recombinant vector for the expression of the respective products: CHO cells for the production of recombinant coagulation factors, for example factor VII, and/or factor VIII, and/or monoclonal antibodies, BHK cells for the production of recombinant erythropoietin, Epstein Barr virus transformed, immortalized human B cells for the production of human antibodies. Useful cell/protein combinations are, for example, CHO cells/coagulation factor VIII, CHO cells/coagulation factor VII, CHO cells/ADAMTS13, CHO cells/furin, and 293 cells/coagulation factor IX.

In a further embodiment of the present invention, the expression of the at least one protein by cells being cultivated in a medium according to the present invention is increased when compared to the expression of the protein by cells not being cultivated in a medium of the present invention. In another embodiment said expression is increased for at least 10%, according to a further embodiment for at least 50%.

The present invention further relates to a method for producing at least one virus or at least one part of a virus, comprising the steps of:
 a) providing a culture of cells;
 b) infecting the cells with at least one virus;
 c) selecting the virus-infected cells; and
 d) propagating the at least one virus in the cells in a medium comprising at least 0.5 mg/L of a polyamine.

In one embodiment of the present invention, the medium of step d) is an oligo-peptide-free medium according to the present invention. In a further embodiment of the present invention, the cells of the culture of step a) have been grown in an oligopeptide-free cell culture medium according to the present invention. In another embodiment, steps a) to d) are conducted in an oligopeptide-free cell culture medium according to the invention.

The virus used in the method according to the invention may be any virus, such as, for example, poxviruses, for example vaccinia or attenuated vaccinia viruses; coronaviruses, for example SARS virus; orthomyxoviruses, for example influenza A or B virus; paramyxoviruses; retroviruses, for example Lenti virus; togaviruses, for example Ross River virus; flaviviruses, for example West Nile virus, Yellow Fever Virus, or FSME virus (i.e. tick borne encephalitis virus); enteroviruses, for example hepatitis A virus; picornaviruses; arenaviruses; herpesviruses'; or adenoviruses. In one embodiment of the present invention, the virus is Modified Vaccinia Virus Ankara (MVA). The virus can be propagated according to the invention for the production of a respective vaccine.

The virus may be a wild-type-virus, an attenuated virus, a reassortant virus, or a recombinant virus or combinations thereof, e.g., attenuated and recombinant. In addition, instead of actual virions being used to infect cells with a virus, an infectious nucleic acid clone may be used. Split virions may also be used.

The method for producing a virus may be used for producing immunogenic compositions comprising a virus, a virus antigen, or a virus-like-particle.

The cells used in the method for producing a virus according to the present invention may be selected from the group consisting of mammalian cells, insect cells, avian cells, bacterial cells, and yeast cells. In one embodiment, the cells used in the method for producing a virus according to the present invention are selected from the group consisting of Vero cells and chicken embryo cells.

Useful combinations of cells with viruses for producing a virus or part of a virus are, for example, Vero cell/attenuated vaccinia, Vero cell/Vaccinia, Vero cell/Hepatitis A, Vero cell/Influenza Virus, Vero cell/West Nile Virus, Vero cell/SARS Virus, Vero cell/Yellow Fever Virus, and chicken embryo cells/FSME virus. In one embodiment of the invention, the cell/virus combination is chicken embryo cells/Modified Vaccinia Virus Ankara (MVA).

Useful cultivation methods include batch-cultivation, feed-batch-cultivation, perfusion cultivation and chemostat-cultivation.

The present invention will now be further illustrated in the following examples, without being limited thereto.

EXAMPLES

Example 1: Preparation of BAV-Medium

Oligopeptide-free medium (BAV-medium) was prepared with basal DMEM/HAM's F12 (1:1) medium comprising inorganic salts, amino acids, vitamins and other components (Life technologies, 32500 Powder). Also added were L-glutamine (600 mg/L), ascorbic acid (20 µM), ethanol amine (25 µM), polyol block-copolymer SYNPERONIC® (SERVA) (0.25 g/L), sodium selenite (50 nM). Additionally essential amino acids were supplemented to the cell culture medium: L-Asparagine.H$_2$O 20 mg/L, L-Cysteine.HCl.H$_2$O 15 mg/L, L-Cystine.2 HCl 20 mg/L, L-Proline 35 mg/L, L-Tryptophan 20 mg/L.

Example 2: Determination of Cell Counts

Cell counts from suspension cells or immobilized cells were determined either by counting with a CASY® cell counter as described by Scharfe et al., Biotechnologie in LaborPraxis 10: 1096-1103 (1988), or by citric acid extraction and fluorescent staining of the nuclei followed by counting with a NucleoCounter® (Chemometec, DK). The specific growth rate (µ) is calculated from the increase of the cell densities ($X_t$) and/or the dilution rate (D) of the steady state of chemostat cultures of suspensions cells over a certain time interval (t):

$$\mu = D + \ln(X_t/X0)/t$$

Example 3: Determination of FVIII Activity

The activity of Factor VIII (FVIII) (cf. FIGS. 1 to 5) was measured by a chromogenic assay (Chromogenic, Sweden).

Example 4: Calculation of the Volumetric (QP) and Cell Specific Productivity (qp)

The volumetric productivity (QP) is calculated from the amount of activity units yielded per liter reactor volume per day (U/L/d) in the production system.

The cell specific productivity (qp) is defined as the specific amount of produced protein (U or μg) per number of cells per day.

Example 5: Large Scale Cell Culture Conditions

Cell cultures of recombinant mammalian cells (e.g., CHO-cells stably expressing Factor VIII, such as GD8/6 cells) were grown in suspension in a chemostat culture in 10 l bioreactors. The culture conditions of 37° C., oxygen saturation 20%, and pH 7.0 to 7.1 were kept constant. The cultures were supplied with a constant feed of BAV-medium.

Example 6: Effect of the Addition of a Polyamine on FVIII Expression

GD8/6 cells were grown in chemostat culture in a 10 L bioreactor as described in Example 5 with a continuous feed of BAV-medium for 11 days, resulting in a decreased productivity of <100 U/L/d. By addition of putrescine.2HCl (2 mg/L) the volumetric FVIII-expression increased by 800% (cf. FIG. 1). Accordingly, putrescine could be clearly identified as the driving factor of cell specific expression for the GD8/6 cell line.

Example 7: Effect of the Addition of a Polyamine and Fe (II) and Cu (II) on FVIII Expression GD8/6 cells were grown in chemostat culture in a 10 L bioreactor as described in Example 5, resulting in an average productivity of 271 U/L/D, with low cell specific productivity and specific growth rates. By addition of Putrescine.2HCl (2 mg/L) the FVIII expression increased to 870 U/L/D, mainly due to an increased cell specific productivity. Additional supplementation with Fe (II) and Cu (II) in a concentration as it is otherwise typically comprised in soy hydrolysates was leading to an increased specific growth rate of approximately 0.60 $d^{-1}$, and an increase of the cell specific productivity to over 1700 mU/10E06 cells/day could be achieved. Under these conditions a volumetric productivity of over 2685 U/L/D was reached. A further increase of the cell density resulted in a volumetric productivity of over 3000 U/L/D. The maximum volumetric productivity of a soy hydrolysate comprising medium under comparable fermentation conditions was 2000 to 2500 U/L/D, indicating that a chemically defined medium comprising only Putrescine and 2 additional metal ions is superior to any soy hydrolysate comprising medium formulation investigated in this process before (cf. FIG. 2).

Example 8: Small Scale Cell Culture Conditions

Small scale experiments with GD8/6 cells in suspension culture were carried out in Techne spinner flasks at 200 ml working volume in batch refeed mode at 37° C., without pH and $pO_2$ control. The cultures were supplied with BAV-medium as defined above additionally supplemented with Putrescine.2HCl, Ornithine.HCl, Spermine.4HCl, or Ethanolamine or combinations thereof in the range of 0-18 mg/L (equivalent to 0-10 mg/L of the biogenic amine without .HCl (cf. FIGS. 3 to 5).

Example 9: Effect of the Addition of Several Polyamines and Combinations of Polyamines on FVIII Expression GD8/6 cells from a culture with BAV-medium as described in Example 8 were centrifuged and transferred to Techne Spinner flasks with a working volume of 200 ml and incubated at a cell density of about 1-2E06 cell/ml with defined medium, supplemented with ethanolamine, putrescine, ornithine, and/or spermine as indicated in FIGS. 3, 4, and 5. Ornithine, which is a precursor of putrescine in the pathway of biogenic amines, could partially substitute putrescine in a concentration-dependent manner. The addition of ornithine at different concentrations to the media comprising putrescine.2HCl resulted in an additional increase of specific FVIII productivities and growth rates (cf. FIG. 3). However, ethanolamine, which is not a polyamine according to the present invention, could neither replace putrescine in any concentration investigated, nor an increase of the ethanolamine concentration in medium comprising putrescine resulted in a significant increase of volumetric productivities or specific growth rates (cf. FIG. 5). A further experiment under similar conditions showed that spermine, another intermediate in the pathway of biogenic amines, could also substitute putrescine in a concentration-dependent manner (cf. FIG. 4).

Example 10: Effect of the Addition of a Polyamine on MVA Virus Production

Primary cell cultures of chicken embryos were cultivated in Techne spinner flasks (working volume 200 ml) using a peptide free medium (FM-Medium) without and with supplementation of 3.6 mg/L Putrescine.2 HCl.

FM medium was prepared with basal M199 medium comprising inorganic salts, amino acids, vitamins and other components (Life technologies, 31150 Powder). Also added were $NaHCO_3$ (ad 4.4 g/L), Gentamycin.SO4 (50 μg/L) and Neomycin.SO4 (50 μg/L).

Figure 6:
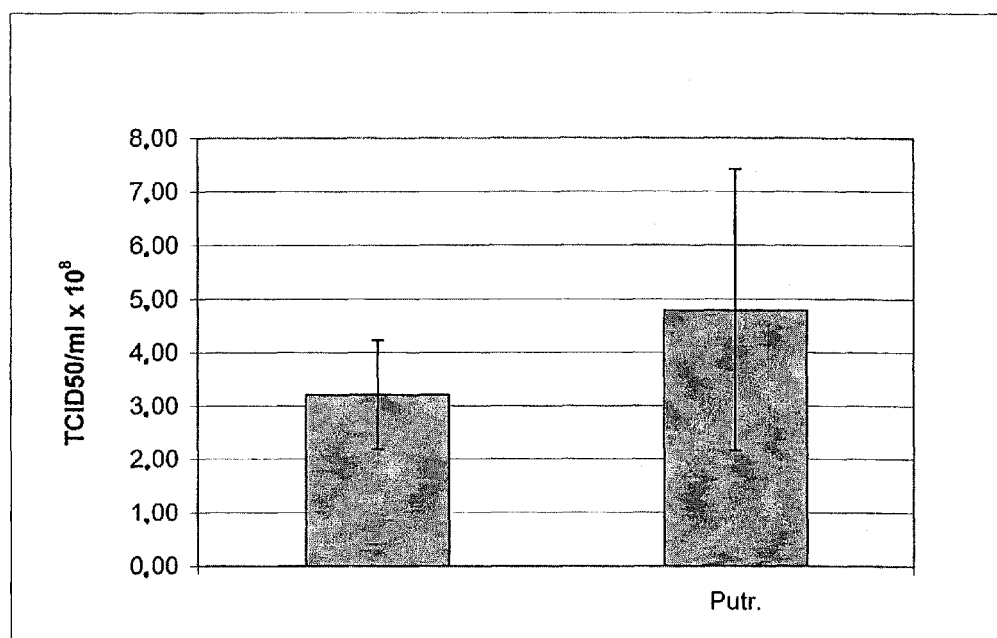
FIG. 6 shows a graph which describes the effect of the addition of 3.6 mg/L putrescine.2HCl on the average MVA virus titer, expressed in $[TCID50/ml \times 10^8]$. -: without addition of Putrescine, Putr.: with addition of 3.6 mg/L putrescine.2HCl.

Cell cultures were infected with MVA virus and supernatants were analysed for virus titer in a TCID50 assay. By the addition of Putrescine, the average virus titer (n=16 samples each) could be increased by approximately 50% (cf. FIG. 6).

Example 11: Effect of the Addition of Several Doses of a Polyamine on MVA Virus Production Primary cell cultures of chicken embryos were cultivated in Techne spinner flasks (working volume 200 ml) using a peptide free medium (CEM-Medium) without and with supplementation of 3.6 and 9 mg/L Putrescine.2 HCl.

CEM medium was prepared with basal DMEM/HAM's F12 (1:1) medium comprising inorganic salts, amino acids, vitamins and other components (Life technologies, 32500 Powder). Also added were $NaHCO_3$ (2 g/L) L-glutamine (600 mg/L), ascorbic acid (20 μM), ethanol amine (25 μM), Synperonic® (SERVA) (0.25 g/L), sodium selenite (50 nM), $FeSO_4.7H_2O$ (600 μg/L), Gentamycin.SO4 (50 μg/L) and Neomycin.SO4 (50 μg/L). Additionally essential amino acids were supplemented to the cell culture medium. Additionally essential amino acids were supplemented to the cell culture medium: L-Asparagine.$H_2O$ 20 mg/L, L-Cysteine.HCl.$H_2O$ 15 mg/L, L-Cystine.2 HCl 20 mg/L, L-Proline 35 mg/L, L-Tryptophan 20 mg/L.

Figure 7:
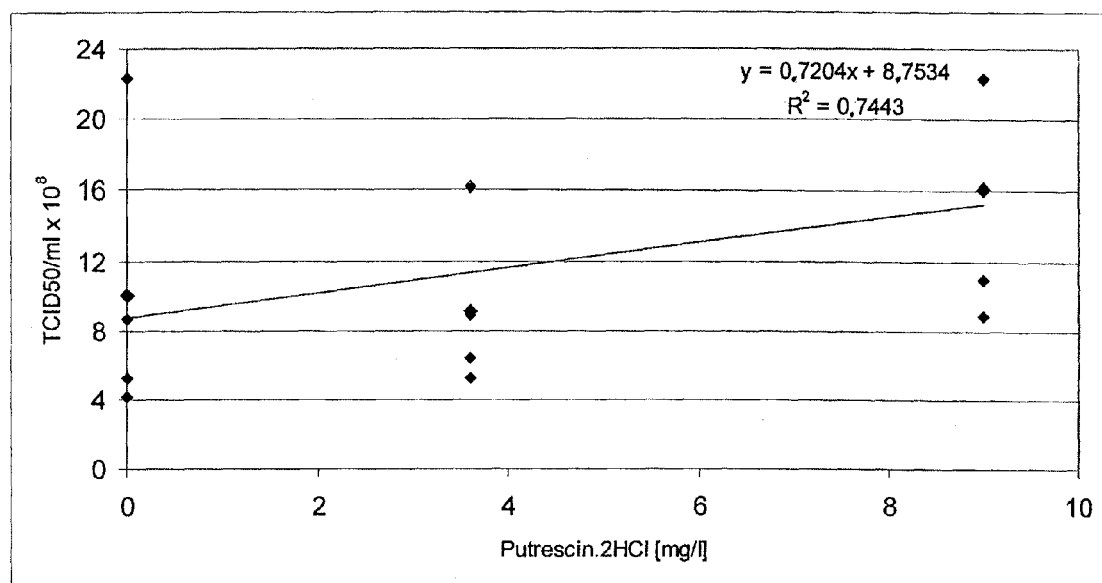
FIG. 7 shows a graph which describes the effect of the addition of various concentrations of putrescine.2HCl, expressed in [mg/l], on the average MVA virus titer, expressed in $[TCID50/ml \times 10^8]$.

Cell cultures were infected with MVA virus and supernatants were analysed for virus titer in a TCID50 assay. By the addition of Putrescine with 9 mg/L, the average virus titer (n=4 samples each) could be increased by approximately 60% (cf. FIG. 7).

It is understood that the examples and embodiments described herein are for illustrative purposes only and that various modifications and changes in light thereof will be suggested to persons skilled in the art and are to be included within the purview of this application and are considered to be within the scope of the appended claims. All publications, patents, and patent applications cited herein are hereby incorporated by reference in their entirety for all purposes.

What is claimed:

1. A method for expressing a coagulation factor VIII protein, comprising the steps of:
   (a) providing a culture of CHO cells;
   (b) introducing at least one nucleic acid sequence comprising a sequence coding for the coagulation factor VIII protein into the cells;
   (c) selecting the cells carrying the nucleic acid sequence; and
   (d) expressing the coagulation factor VIII protein in a chemically defined protein-free medium that does not comprise oligopeptides, the medium comprising DMEM:HAM's F12 (1:1) basal medium, putrescine at a concentration of at least 1 mg/L, and Fe(II) and Cu(II) at a level greater than the amount in basal DMEM:HAM's F12 (1:1), wherein the medium is supplemented with L-glutamine, ascorbic acid, ethanolamine, sodium selenite, and a non-ionic surfactant, wherein the cells are cultivated by chemostat cultivation.

2. The method of claim 1, wherein the medium further comprises a polyamine selected from the group consisting of cadaverine, spermidine, spermine, agmatine, ornithine, or combinations thereof.

3. The method of claim 1, wherein the medium comprises ornithine, spermine, or combinations thereof.

4. The method of claim 1, wherein the putrescine is synthetically produced.

5. The method of claim 1, wherein the putrescine originates from a source other than a protein hydrolysate.

6. The method of claim 1, wherein the medium is further supplemented with L-Asparagine, L-Cysteine, L-Cystine, L-Proline, and L-Tryptophan.

7. The method of claim 1, wherein the medium comprises putrescine at a concentration of from about 1.0 mg/L to about 20 mg/L.

8. The method of claim 1, wherein the non-ionic surfactant comprises copolymers or mixtures of polyethylene glycols and polypropylene glycols.

9. The method of claim 1, wherein the medium further comprises a buffer substance.

10. The method of claim 9, wherein the buffer substance comprises one or more of sodium bicarbonate, antioxidants, stabilizers, or protease inhibitors.

* * * * *